(12) United States Patent
Ziemer et al.

(10) Patent No.: US 7,867,623 B2
(45) Date of Patent: Jan. 11, 2011

(54) POLYMERIC PARTICLES CAPABLE OF ABSORBING BLOOD AND/OR BODY FLUIDS

(75) Inventors: Antje Ziemer, Mannheim (DE); Bernhard Steinmetz, Limburgerhof (DE); Michael Demarco, Weinheim (DE); Monika Medelnick, Altrip (DE)

(73) Assignee: BASF Aktiengesellschaft

( * ) Notice: Subject to any disclaimer, the term of this patent is extended or adjusted under 35 U.S.C. 154(b) by 1262 days.

(21) Appl. No.: 10/577,028

(22) PCT Filed: Oct. 28, 2004

(86) PCT No.: PCT/EP2004/012178

§ 371 (c)(1), (2), (4) Date: Apr. 25, 2006

(87) PCT Pub. No.: WO2005/042042

PCT Pub. Date: May 12, 2005

(65) Prior Publication Data

US 2007/0112222 A1 May 17, 2007

(30) Foreign Application Priority Data

Oct. 31, 2003 (DE) ............................. 103 51 267
Jun. 28, 2004 (DE) ....................... 10 2004 035 671

(51) Int. Cl.
B32B 27/00 (2006.01)
(52) U.S. Cl. .................. 428/500; 428/521; 524/556; 525/7; 525/327.4; 525/191; 525/193; 526/317.1; 604/358; 604/370; 604/378
(58) Field of Classification Search .............. 604/358, 604/370, 378; 526/317.1; 428/500, 521; 524/556; 525/7, 191, 193, 327.4
See application file for complete search history.

(56) References Cited

U.S. PATENT DOCUMENTS

| 4,734,478 A | 3/1988 | Tsubakimoto et al. |
| 5,322,896 A | 6/1994 | Ueda et al. |
| 5,961,504 A | 10/1999 | Gross |
| 6,284,362 B1 | 9/2001 | Takai et al. |
| 6,620,889 B1 | 9/2003 | Mertens et al. |
| 6,916,864 B2 * | 7/2005 | Gartner et al. ............ 523/337 |
| 2003/0035783 A1 * | 2/2003 | Birkel et al. ............. 424/70.2 |
| 2003/0207997 A1 | 11/2003 | Mertens et al. |
| 2005/0153123 A1 * | 7/2005 | Herfert et al. ............ 428/327 |
| 2007/0167560 A1 * | 7/2007 | Smith et al. ............... 524/556 |
| 2007/0254177 A1 * | 11/2007 | Smith et al. ............... 428/521 |

FOREIGN PATENT DOCUMENTS

| DE | 96 965 | 4/1973 |
| DE | 199 09 653 | 9/2000 |
| EP | 0 001 706 A1 | 5/1979 |
| EP | 0 009 977 A1 | 4/1980 |
| EP | 0 071 063 A1 | 2/1983 |
| EP | 0 317 106 A2 | 5/1989 |
| EP | 0 509 708 A1 | 10/1992 |
| EP | 0 759 460 A1 | 2/1997 |
| EP | 759460 | 2/1997 |
| EP | 1 165 631 A1 | 1/2002 |
| JP | 57-168921 A | 10/1982 |
| JP | 58-032641 A | 2/1983 |
| JP | 61-016903 A | 1/1986 |
| JP | 62007745 A | 1/1987 |
| JP | 2153903 A | 6/1990 |
| JP | 06-345980 | 12/1994 |
| WO | WO-95/19191 | 7/1995 |
| WO | WO-99/03577 A1 | 1/1999 |
| WO | WO-99/55767 | 11/1999 |
| WO | WO-00/10496 | 3/2000 |
| WO | WO-01/70287 A2 | 9/2001 |

OTHER PUBLICATIONS

U.S. Appl. No. 09/674,263, filed Oct. 30, 2000.

* cited by examiner

Primary Examiner—Charles I Boyer
(74) Attorney, Agent, or Firm—Marshall, Gerstein & Borun LLP

(57) ABSTRACT

Polymeric particles capable of absorbing blood and/or body fluids, the polymeric particles being coated with at least one surfactant and with at least one solvent, are produced and used for absorbing blood and/or body fluids, especially in hygiene articles.

7 Claims, No Drawings

POLYMERIC PARTICLES CAPABLE OF ABSORBING BLOOD AND/OR BODY FLUIDS

CROSS-REFERENCE TO RELATED APPLICATIONS

This is the U.S. national phase application of International Application No. PCT/EP2004/012178, filed Oct. 28, 2004, which claims the benefit of German patent application No. 10 2004 035 671.8, filed Jun. 28, 2004, and German patent application No. 103 51 267.5, filed Oct. 31, 2003.

The present invention relates to polymeric particles capable of absorbing blood and/or body fluids, a process for producing said polymeric particles and to their use for absorbing blood and/or body fluids, especially in hygiene articles.

Polymers capable of absorbing fluids are known as superabsorbent polymers (SAPs) or superabsorbents, and are in particular polymers of (co)polymerized hydrophilic monomers, graft copolymers of one or more hydrophilic monomers on a suitable grafting base, crosslinked ethers of cellulose or of starch, crosslinked carboxymethylcellulose, partially crosslinked polyalkylene oxide or natural products which are swellable in aqueous fluids, examples of such natural products being guar derivatives. Such polymers are used as products capable of absorbing aqueous solutions to manufacture diapers, tampons, sanitary napkins and other hygiene articles, but also as water-retaining agents in market gardening or to thicken all kinds of wastes, especially medical wastes.

Polymers capable of absorbing fluids are preferably capable of absorbing at least 10 times their own weight and preferably 20 times their own weight, based on polymer used, of 0.9% by weight sodium chloride solution. This absorption is preferably achieved even under a pressure of 0.7 psi for example.

Polymers capable of absorbing fluids are typically surface or gel postcrosslinked to improve their performance characteristics.

This postcrosslinking is known per se to one skilled in the art and preferably takes place in an aqueous gel phase or as surface postcrosslinking of ground and classified polymeric particles.

Conventional superabsorbents are optimized to absorb urine in hygiene articles, especially baby diapers. They always absorb substantially less blood compared with synthetic urine or physiological saline.

It is therefore advantageous to provide a superabsorbent which is capable of absorbing larger amounts of blood than commercially available superabsorbents. Such superabsorbents are preferentially useful in feminine hygiene products.

Rapid blood absorbence is desirable for feminine hygiene products in order that the fluid be rapidly transported away from the body and stored in the hygiene article. High retention is needed as well as rapid absorption and a high rate of swell.

Higher blood absorbence is a significant advantage for hygiene articles, since this permits the development of very effective and thin hygiene articles, which are preferred by the customer because of the wear comfort.

WO-A-99/55767 describes the use of aluminates for surface postcrosslinking of uncrosslinked or covalently crosslinked hydrogels. The reference teaches that the subsequent crosslinking improves gel strength and the absorption of fluids and blood, especially the absorbency under load value.

DE-A-199 09 653 teaches the application of an aqueous solution of a cation before or after a postcrosslinking reaction.

WO-A-00/10496 describes an optimized material for absorbing blood by application of kaolinite to moistened superabsorbent and subsequent drying.

EP-A-0 759 460 describes a material which was postcrosslinked again by addition of large amounts of a surface-postcrosslinking reagent. However, the higher degree of crosslinking does not lead to products having very high blood absorbence.

WO-A-95/19191 describes the production of superabsorbent materials having enhanced blood absorbence. Commercially available superabsorbents are additionally sprayed with polyols, such as polyethylene glycol or glycerol for example. The additional crosslinking of the polymer strands is essentially through hydrogen bonds. As exemplified therein, blood absorbence cannot be further increased by using a larger amount. On the contrary, blood absorbence goes back down as dose increases.

JP-A-06/345980 describes mixing superabsorbents with anionic surfactants. This does not enhance blood absorbence, nor does it increase the rate of absorption.

The present invention therefore had for its object to develop a superabsorbent having improved blood absorbence.

The present invention further has for its object to provide a process which leads in simple steps to superabsorbents having improved blood absorbence.

The present invention further has for its object to provide a process for producing superabsorbents from commercially available superabsorbents.

We have found that this object is achieved by providing absorbing polymeric particles comprising a) at least one interpolymerized ethylenically unsaturated acid-functional monomer, b) at least one interpolymerized crosslinker, c) if appropriate one or more interpolymerized ethylenically and/or allylically unsaturated monomers copolymerizable with a), d) if appropriate one or more water-soluble polymers onto which said monomers a), b) and if appropriate c) are at least partially grafted, and e) if appropriate one or more reacted postcrosslinkers, wherein said polymeric particles are coated with at least one surfactant and with at least one solvent of the general formula I

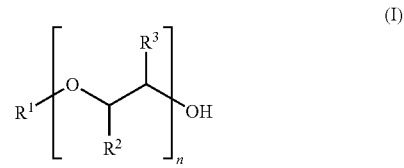

where $R^1$ is $C_1$-$C_8$-alkyl with or without halogen substitution, $R^2$, $R^3$ are independently hydrogen or methyl, and n is an integer from 0 to 5.

The at least one surfactant can be an anionic, cationic and/or nonionic surfactant. Nonionic surfactants are preferred, especially nonionic surfactants having an HLB value in the range from 2 to 18. The HLB value is a measure of the water- or oil-solubility of predominantly nonionic surfactants and can be determined by customary methods.

A surfactant consists of at least one polar group and at least one apolar group. Preferred surfactants comprise large apolar and/or polar groups. Large groups are groups having a molecular weight of not less than 130 g/mol, preferably not less than 250 g/mol and more preferably not less than 500 g/mol.

Useful surfactants include for example sorbitan esters, such as sorbitan monostearate, sorbitan monooleate, sorbitan palmitate and sorbital laurate, and also glyceryl esters whose acid component derives from $C_{14}$- to $C_{20}$-carboxylic acids.

Preferred surfactants are alkoxylated, preferably ethoxylated, $C_8$-$C_{20}$-alcohols, which alcohols may be branched and/or unsaturated, and also alkoxylated, preferably ethoxylated, sorbitan monoesters, such as sorbitan monostearate and sorbitan monooleate.

The viscosity of the at least one surfactant is preferably above 20 mpas, more preferably above 25 mPas and most preferably above 30 mPas (measured at 23° C. in accordance with EN12092).

Preferred solvents are alcohols or alkoxylated alcohols of the general formula I where $R^1$ is $C_2$-$C_6$-alkyl, $R^2$, $R^3$ are each hydrogen, and n is an integer from 1 to 3.

Very particularly preferred solvents are alkoxylated alcohols of the general formula I where $R^1$ is $C_3$-$C_5$-alkyl, $R^2$, $R^3$ are each hydrogen, and n is 2.

Illustrative examples of solvents include ethylene glycol monoethyl ether, ethylene glycol mono-n-propyl ether, ethylene glycol monoisopropyl ether, ethylene glycol mono-n-butyl ether, ethylene glycol mono-sec-butyl ether, ethylene glycol monoisobutyl ether, ethylene glycol mono-tert-butyl ether, ethylene glycol mono-n-pentyl ether, ethylene glycol mono-sec-pentyl ether, ethylene glycol monoisopentyl ether, ethylene glycol mono-tert-pentyl ether, ethylene glycol mono-n-hexyl ether, diethylene glycol monoethyl ether, diethylene glycol mono-n-propyl ether, diethylene glycol monoisopropyl ether, diethylene glycol mono-n-butyl ether, diethylene glycol mono-sec-butyl ether, diethylene glycol monoisobutyl ether, diethylene glycol mono-tert-butyl ether, diethylene glycol mono-n-pentyl ether, diethylene glycol mono-sec-pentyl ether, diethylene glycol monoisopentyl ether, diethylene glycol mono-tert-pentyl ether, diethylene glycol mono-n-hexyl ether, triethylene glycol monoethyl ether, triethylene glycol mono-n-propyl ether, triethylene glycol monoisopropyl ether, triethylene glycol mono-n-butyl ether, triethylene glycol mono-sec-butyl ether, triethylene glycol monoisobutyl ether, triethylene glycol mono-tert-butyl ether, triethylene glycol mono-n-pentyl ether, triethylene glycol mono-sec-pentyl ether, triethylene glycol monoisopentyl ether, triethylene glycol mono-tert-pentyl ether and triethylene glycol mono-n-hexyl ether.

The viscosity of the at least one solvent is preferably less than 20 mPas, more preferably less than 15 mPas and most preferably less than 10 mPas (measured at 23° C. in accordance with EN12092). Further solvents can be used in addition.

In a preferred embodiment the absorbent polymeric particles are further coated with multivalent metal cations, aluminum cations being particularly preferred.

The polymeric particles of the present invention typically have a blood absorbence (as measured using dry polymeric particles) of not less than 15 g/g, preferably not less than 20 g/g, more preferably not less than 25 g/g, even more preferably not less than 27 g/g and most preferably not less than 29 g/g.

The present invention further provides a process for aftertreating absorbent polymers that comprises the steps of
aftertreating with at least one anionic, cationic and/or nonionic surfactant, preferably with a nonionic surfactant having an HLB value in the range from 2 to 18.
aftertreating with at least one solvent of the general formula I where $R^1$, $R^2$, $R^3$ and n are each as defined above, preferably with diethylene glycol monobutyl ether.

The two steps are typically carried out concurrently. It is preferable to spray a solution of the surfactant in the solvent onto the dried and classified superabsorbents. Not only is the surfactant more uniformly disbursed as a result, but blood absorbence improves as well.

The present invention further provides a process for aftertreating absorbent hydrogels that comprises the steps of
aftertreating with at least one multivalent metal cation, solutions of multivalent metal cations, for example $A^{3+}$, $Fe^{2+}$, $Fe^{3+}$, $Ti^{3+}$, $Ti^{4+}$, $Co^{2+}$, $Ni^{2+}$, $Cr^{3+}$, $Mn^{2+}$, $Zn^{2+}$, $Mg^{2+}$, $Ca^{2+}$, $Zr^{3+}$, $Zr^{4+}$, more preferably $A^{3+}$.
aftertreating with at least one anionic, cationic and/or nonionic surfactant, preferably with a nonionic surfactant having an HLB value in the range from 2 to 18.
aftertreating with at least one solvent of the general formula I, preferably with diethylene glycol monobutyl ether.

The last two steps are typically carried out concurrently.

The amount of surfactant used is typically in the range from 0.01% to 5% by weight, preferably in the range from 0.05% to 4% by weight and more preferably in the range from 0.1% to 3% by weight, based on absorbent polymer.

The amount of solvent of the general formula I is typically in the range from 0.1% to 10% by weight, preferably in the range from 0.5% to 7% by weight and more preferably in the range from 1% to 5% by weight, based on absorbent polymer.

The surfactants are preferably metered as a solution in the solvent. The concentration of surfactant in the solution is typically in the range from 5% to 80% by weight, preferably in the range from 15% to 60% by weight and more preferably in the range from 20% to 55% by weight.

When multivalent metal cations are used, the amount of multivalent metal cation used will be typically in the range from 0.01% to 4% by weight, preferably in the range from 0.05% to 3% by weight and more preferably in the range from 0.1% to 1% by weight, based on absorbent polymer.

The counterions to the multivalent metal ions are not subject to any restriction, but when a solvent is used there is a preference for counterions which ensure adequate solubility, preference being given to sulfate. The metal cations are preferably metered as a solution. Water is a particularly preferred solvent. The concentration of multivalent metal cation in the solution is typically in the range from 1% to 10% by weight, preferably in the range from 2% to 8% by weight and more preferably in the range from 3% to 6% by weight.

The order in which the aftertreating agents are metered is not subject to any restriction, but multivalent metal cations are preferably metered before surfactants.

The dissolved aftertreating agents are preferably sprayed onto the dried water-absorbing polymer and mixed. The type of mixing is not subject to any restrictions, but preference is given to using reaction mixers or mixing and drying ranges, such as for example Lbdige® mixers, BEPEX® mixers, NAUTA® mixers, SCHUGGI® mixers, NARA® dryers and PROCESSALL®. Fluidized bed dryers can also be used moreover. The mixing is advantageously carried out using a residence time from 1 to 180 minutes and preferably from 2 to 15 minutes and a speed from 10 to 1000 rpm and preferably from 50 to 250 rpm.

The last step may be followed by drying. Drying may take place in the mixer itself, by heating the jacket or introducing a stream of warm air. It is similarly possible to use a downstream dryer, such as for example a tray dryer, a rotary tube oven or a heatable screw. But it is also possible for example to utilize an azeotropic distillation as a drying process.

Preferred drying temperatures in the process of the present invention are in the range from 50 to 250° C., preferably in the range from 50 to 200° C. and more preferably in the range from 50 to 180° C. The residence time at this temperature in the reaction mixer or dryer is advantageously below 30 minutes and preferably below 10 minutes.

The drying is preferably carried out at reduced pressure, preferably at less than 500 mbar and more preferably at less than 200 mbar and, if appropriate, supported by a dry gas stream, preferably nitrogen, in an amount from 20 to 1000 l/kgh and preferably from 100 to 250 l/kgh.

The present invention further provides crosslinked water-absorbing polymers obtainable by the process of the present invention, especially absorbent hydrogels having a blood absorbence of not less than 15 g/g, preferably not less than 20 g/g, more preferably not less than 25 g/g and most preferably in the range from 29 to 40 g/g and also their use for absorbing blood and/or body fluids, especially in hygiene articles.

The present invention further provides hygiene articles comprising the superabsorbent of the present invention.

The absorbing polymers which can be used in the process of the present invention are in particular polymers of crosslinked (co)polymerized hydrophilic monomers, polyaspartic acid, graft (co)polymers of one or more hydrophilic monomers on a suitable grafting base, crosslinked cellulose ethers, crosslinked starch ethers or natural products which are swellable in aqueous fluids, such as guar derivatives for example. Preferably, the polymer to be crosslinked is a polymer which comprises structure units which derive from acrylic acid or esters thereof or which were obtained by graft copolymerization of acrylic acid or acrylic esters on a water-soluble polymeric matrix. These hydrogels will be known to one skilled in the art and are described for example in U.S. Pat. No. 4,286,082, DE-C-27 06 135, U.S. Pat. No. 4,340,706, DE-C-37 13 601, DE-C-28 40 010, DE-A-43 44 548, DE-A-40 20 780, DE-A-40 15 085, DE-A-39 17 846, DE-A-38 07 289, DE-A-35 33 337, DE-A-35 03 458, DE-A42 44 548, DE-A-42 19 607, DE-A-40 21 847, DE-A-38 31 261, DE-A-35 11 086, DE-A-31 18 172, DE-A-30 28 043, DE-A-44 18 881, EP-A-0 801 483, EP-A-0 455 985, EP-A-0 467 073, EP-A-0 312 952, EP-A-0 205 874, EP-A-0 499 774, DE-A 26 12 846, DE-A-40 20 780, EP-A-0 205 674, U.S. Pat. No. 5,145,906, EP-A-0 530 438, EP-A-0 670 073, U.S. Pat. No. 4,057,521, U.S. Pat. No. 4,062,817, U.S. Pat. No. 4,525,527, U.S. Pat. No. 4,295,987, U.S. Pat. No. 5,011,892, U.S. Pat. No. 4,076,663 or U.S. Pat. No. 4,931,497.

Examples of hydrophilic monomers suitable for preparing these absorbing polymers are acids which are capable of addition polymerization, such as acrylic acid, methacrylic acid, vinylsulfonic acid, vinylphosphonic acid, maleic acid, maleic anhydride, fumaric acid, itaconic acid, 2-acrylamido-2-methylpropanesulfonic acid, 2-acrylamido-2-methylpropanephosphonic acid and also their amides, hydroxyalkyl esters and amino- or ammonio-containing esters and amides and also the alkali metal and/or ammonium salts of the acid-functional monomers. It is further possible to use water-soluble N-vinylamides such as N-vinylformamide or else diallyldimethylammonium chloride. Preferred hydrophilic monomers are compounds of the general formula II

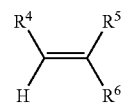

(II)

where
$R^4$ is hydrogen, methyl, ethyl or carboxyl,
$R^5$ is —$COOR^7$, hydroxysulfonyl or phosphonyl, a phosphonyl group esterified with a $C_1$-$C_4$-alkanol, or a group of the formula III

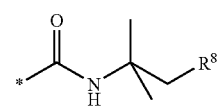

(III)

$R^6$ is hydrogen, methyl or ethyl,
$R^7$ is hydrogen, $C_1$-$C_4$-aminoalkyl, $C_1$-$C_4$-hydroxyalkyl, alkali metal ion or ammonium ion, and
$R^8$ is a sulfonyl group, a phosphonyl group or a carboxyl group or a respective alkali metal or ammonium salt.

Examples of $C_1$-$C_4$-alkanols are methanol, ethanol, n-propanol, isopropanol or n-butanol.

Particularly preferred hydrophilic monomers are acrylic acid and methacrylic acid and also their alkali metal or ammonium salts, for example sodium acrylate, potassium acrylate or ammonium acrylate.

Suitable grafting bases for absorbing polymers which are obtainable by graft copolymerization of olefinically unsaturated acids or their alkali metal or ammonium salts can be of natural or synthetic origin. Examples are starch, cellulose or cellulose derivatives and also other polysaccharides and oligosaccharides, polyalkylene oxides, especially polyethylene oxides and polypropylene oxides, and also hydrophilic polyesters.

Suitable polyalkylene oxides have for example the formula IV

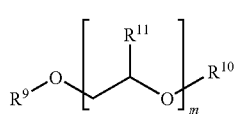

(IV)

where
$R^9$, $R^{10}$ are independently hydrogen, alkyl, alkenyl or aryl,
$R^{11}$ is hydrogen or methyl, and
m is an integer from 1 to 10 000.
$R^9$ and $R^{10}$ are each preferably hydrogen, $C_1$-$C_4$-alkyl, $C_2$-$C_6$-alkenyl or phenyl.

Preferred absorbing polymers are in particular polyacrylates, polymethacrylates and also the U.S. Pat. No. 4,931,497, U.S. Pat. No. 5,011,892 and U.S. Pat. No. 5,041,496 graft polymers.

The absorbing polymers have preferably been crosslinked, i.e., they comprise compounds having at least two double bonds which have been polymerized into the polymeric network. Suitable crosslinkers are in particular N,N'-methylenebisacrylamide and N,N'-methylenebismethacrylamide, esters of unsaturated mono- or polycarboxylic acids of polyols, such as diacrylate or triacrylate, for example butanediol or ethylene glycol diacrylate or methacrylate and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. The process of the present invention can further utilize hydrogels which are prepared using polyallyl ethers as a crosslinker and by acidic homopolymerization of acrylic acid. Suitable crosslinkers are pentaerythritol triallyl and tetraallyl ethers, polyethylene glycol diallyl ether, ethylene glycol diallyl ether, glycerol diallyl ether, glycerol triallyl ether, polyallyl ethers based on sorbitol, and also ethoxylated variants thereof.

The preferred methods of making the base polymer which can be used in the process of the present invention are described in "Modern Superabsorbent Polymer Technology", F. L. Buchholz and A. T. Graham, Wiley-VCH, 1998, pages 77 to 84. Particular preference is given to base polymers which are prepared in a kneader, as described for example in WO-A-01/38402, or on a belt reactor, as described for example in EP-A-0 955 086.

The absorbing polymer is preferably a polymeric acrylic acid or a polyacrylate. This water-absorbing polymer can be prepared by a process known from the literature. Preference is given to polymers which comprise crosslinking comonomers in amounts from 0.001 to 10 mol % and preferably 0.01 to 1 mol %, but very particular preference is given to polymers which were obtained by free-radical polymerization and where a polyfunctional ethylenically unsaturated free-radical crosslinker was used which additionally bears at least one free hydroxyl group (such as for example pentaerythritol triallyl ether or trimethylolpropane diallyl ether).

The absorbing polymers are preparable by addition polymerization processes known per se. Preference is given to addition polymerization in aqueous solution conducted as a gel polymerization. It involves for example 15% to 50% by weight aqueous solutions of one or more hydrophilic monomers and if appropriate of a suitable grafting base being addition polymerized in the presence of a free-radical initiator by utilizing the Trommsdorff-Norrish effect (Makromol. Chem. 1, 169 (1947)), preferably without mechanical mixing. The addition polymerization reaction may be carried out in the temperature range between 0 and 150° C. and preferably between 10 and 100° C., not only at atmospheric pressure but also at superatmospheric or reduced pressure. As usual, the polymerization can also be carried out in a protective gas atmosphere, preferably under nitrogen. The addition polymerization may be induced using high-energy electromagnetic rays or the customary chemical addition polymerization initiators, for example organic peroxides, such as benzoyl peroxide, tert-butyl hydroperoxide, methyl ethyl ketone peroxide, cumene hydroperoxide, azo compounds such as azodiisobutyronitrile and also inorganic peroxo compounds such as $(NH_4)_2S_2O_8$ or $K_2S_2O_8$ or $H_2O_2$. They may be used if appropriate in combination with reducing agents such as sodium hydrogensulfite and iron(II) sulfate or redox systems, where the reducing component included is an aliphatic or aromatic sulfinic acid, such as benzenesulfinic acid and toluenesulfinic acid or derivatives of these acids, such as Mannich adducts of sulfinic acids, aldehydes and amino compounds, as described in DE-A-13 01 566. The performance characteristics of the polymers can be further improved by postheating the polymer gels in the temperature range from 50 to 130° C. and preferably from 70 to 100° C. for several hours.

The hydrogels obtained are neutralized for example to 0 to 100 mol % preferably 25 to 100 mol % and more preferably to 50 to 85 mol %, based on monomer used, for which the customary neutralizing agents can be used, preferably alkali metal hydroxides, alkali metal oxides, but more preferably sodium hydroxide, sodium carbonate and sodium bicarbonate.

Neutralization is typically achieved by mixing the neutralizing agent as an aqueous solution or else preferably as a solid into the gel. For this, the gel is mechanically comminuted, for example by means of a meat grinder, and the neutralizing agent is sprayed on, scattered on or poured on and then carefully mixed in. The gel mass obtained can then be repeatedly passed through the meat grinder for homogenization. The neutralized gel mass is then dried with a belt or can dryer until the residual moisture content is preferably below 10% by weight and especially below 5% by weight. The dried hydrogel is subsequently ground and sieved, and the grinding can typically be carried out using roll mills, pin mills or swing mills. The particle size of the sieved hydrogel is typically below 1000 µm, frequently below 700 µm, preferably below 500 µm, more preferably below 400 µm and most preferably below 300 µm, the fraction of particles less than 10 µm being below 1% by weight. The 45 to 250 µm sieve cut is very particularly preferred.

Smaller particle sizes lead to higher blood absorbence in particular.

The postcrosslinking is typically carried out by spraying a solution of the surface postcrosslinker onto the hydrogel or dry base polymer powder. After spraying, the polymeric powder is thermally dried, and the crosslinking reaction can take place not only before but also during the drying.

The spraying with a solution of the crosslinker is preferably carried out in reaction mixers or mixing and drying ranges, such as for example Lödige® mixers, BEPEX® mixers, NAUTA® mixers, SCHUGGI® mixers, NARA® dryers and PROCESSALL®. Fluidized bed dryers can be used as well in addition.

Drying may take place in the mixer itself, by heating the jacket or introducing a stream of warm air. It is similarly possible to use a downstream dryer, such as for example a tray dryer, a rotary tube oven or a heatable screw. But it is also possible for example to utilize an azeotropic distillation as a drying process.

Preferred drying temperatures are in the range from 50 to 250° C., preferably in the range from 50 to 200° C. and more preferably in the range from 50 to 150° C. The preferred residence time at this temperature in the reaction mixer or dryer is below 30 minutes and more preferably below 10 minutes.

The crosslinker is preferably dissolved in solvents which are not self-reactive, preferably in lower alcohols, such as for example methanol, ethanol, propanediol, ethylene glycol, most preferably in aqueous solutions of such suitable alcohols, in which case the alcohol content of the solution is in the range from 10% to 90% by weight and more preferably in the range from 40% to 60% by weight.

The crosslinker is used in an amount from 0.01% to 1% by weight, based on the polymer used, and the crosslinker solution itself is used in an amount from 1% to 20% by weight and preferably from 5% to 15% by weight, based on the polymer used.

Non-postcrosslinked hydrogel-forming polymers (base polymers) are particularly suitable for the process of the present invention. The process of the present invention therefore preferably utilizes mixtures comprising a high fraction of base polymer or utilizes pure base polymer. The fraction of nbn-postcrosslinked polymeric particles in the mixture is typically not less than 20% by weight, preferably not less than 50% by weight and more preferably not less than 70% by weight.

The present invention's polymeric particles capable of absorbing fluids are particularly useful for absorbing blood and/or body fluids in hygiene articles, for example incontinence articles, napkins, tampons, liners. To this end, the present invention's polymeric particles can be processed with fibers, such as cellulose for example, and also fibrous web to form absorbing composites.

It will be appreciated that, as or when required, the polymeric particles may have added to them further materials, such as bactericides, biocides, scents, stabilizers, dyes, indicators, defoamers, complexing agents, wetting agents, thickeners, dispersions, plasticizers, retention aids, pigments, fillers and further auxiliaries known to one of ordinary skill in the art.

Useful fillers include for example sand or clay minerals as described in WO-A-04/018005 at pages 16 to 20. The fillers' particle size is typically in the range from 10 to 1000 µm, preferably in the range from 150 to 850 µm and more preferably in the range from 300 to 600 µm. Particle size can be adjusted by customary methods via corresponding sieved fractions. Preferably, the polymeric particles of the present invention and the fillers have similar particle sizes, which prevents separation.

In addition, for example, radiation- and/or heat-curable materials (crosslinkers) and/or hydrophobicizers can be added. Useful hydrophobicizers include customary aqueous paraffin dispersions or silicones.

Another advantage with the process of the present invention is that the polymeric particles capable of absorbing blood and/or body fluids are available by simple steps from superabsorbents available commercially and hence inexpensively in large volumes.

To determine the quality of the present invention's aftertreatment, the polymeric particles of the present invention are tested using test methods described hereinbelow:

Methods:

Measurements should be carried out, unless otherwise stated, at an ambient temperature of 23±2° C. and a relative humidity of 50±10%. The swellable hydrogel-forming polymer is thoroughly mixed through prior to measurement.

Blood Absorbence (BA):

This method is used to determine the blood absorbence of absorbing polymers within 30 minutes.

Experimental Setup:
plastics container, round, internal diameter 50±0.2 mm, internal height 20±0.2 mm (container 1)
plastics cylinder with net (400 mesh=36 µm size holes), internal diameter 25±0.2 mm, height 40±0.2 mm (container II)
petri dish with lid, diameter 140 mm, height 75 mm
stopwatch
analytical balance accurate to ±0.0001 g
defibrinated sheep blood from Oxoid GmbH, D46467 Wesel Procedure:

0.2 g of absorbing polymer is weighed into container II, the empty weight of which was determined beforehand. Container I is charged with 15 g of defibrinated sheep blood. Container II is then placed in container I, and this setup is placed in the petri dish, the petri dish is sealed with the lid and the stopwatch is started. After 30 minutes, container II is removed from container I, the outside of container II is cleaned with a cloth and the weight of container II is subsequently determined. The difference between this weight and the empty weight of container II and also the mass of polymer used (0.2 g) is used to compute the amount of blood absorbed and hence the blood absorbence.

Calculation:

$$\frac{\text{blood absorbed [g]}}{\text{weight of absorbing polymers [g]}} = \text{blood absorbence [g/g]}$$

The test was carried out with the moist or dried absorbing polymer.

Centrifuge Retention Capacity (CRC)

This method measures the free swell capacity of the absorbing polymer in a teabag. To measure CRC, 0.2000±0.0050 g of absorbing polymer is weighed in a teabag 60×85 mm in size, which is subsequently sealed. The teabag is placed for 30 minutes in an excess of 0.9% by weight sodium chloride solution (at least 0.83 l of sodium chloride solution/1 g of polymeric powder). The teabag is subsequently centrifuged at 250 G for 3 minutes. The amount of liquid retained by the hydrogel is determined by weighing back the centrifuged teabag.

Centrifuge Retention Capacity can also be determined by the centrifuge retention capacity test method no.441.2-02 recommended by EDANA (European Disposables and Nonwovens Association).

Free Swell Capacity (FSC):

This method likewise measures the free swell capacity of the absorbing polymer in a teabag. The method is carried out similarly to determining Centrifuge Retention Capacity except that the teabag is not centrifuged. Instead, the teabag is allowed to drip for 10 minutes by hanging it up at one corner.

Free Swell Capacity can also be determined by the free swell capacity test method no. 440.2-02 recommended by EDANA (European Disposables and Nonwovens Association).

EXAMPLES

Examples 1 to 10

A Lödige® plowshare M5/20 laboratory batch mixer was charged with 1 kg of commercially available polymer capable of absorbing aqueous fluids (Hysorb F). The stated amount of surfactant solution, based on absorbing polymer, was sprayed on as a 50% by weight solution in diethylene glycol monobutyl ether and mixed in for 10 minutes.

if appropriate the stated amount of aluminum sulfate solution, based on absorbing polymer, was sprayed on as a 26.8% by weight aqueous solution and mixed in for 10 minutes and Mixer speed was 125 rpm.

In those examples in which the aqueous aluminum sulfate solution was sprayed on, additional drying was carried out. Drying was done at 70° C., at a pressure of 150 mbar in the course of a residence time of 16 hours. Drying was augmented by a gas stream of 200 l/h of nitrogen.

The results are summarized in the tables which follow.

TABLE 1

Addition of cation solutions

| Example | Surfactant solution | Cation solution | BA, moist [g/g] | BA, dry [g/g] | FSC, moist [g/g] | FSC, dry [g/g] | CRC, moist [g/g] | CRC, dry [g/g] |
|---|---|---|---|---|---|---|---|---|
| 1 | 5% Lutensol ® XP 30 | | 18.2 | 20.1 | 33.1 | 36.1 | 25.5 | 27.6 |
| 2 | 5% Lutensol ® XP 30 | 4% $Al_2(SO_4)_3$ | 25.8 | 29.0 | 43.2 | 47.2 | 19.2 | 22.9 |
| 3 | 5% Lutensol ® XL 30 | | 27.7 | 20.1 | 34.5 | 38.1 | 26.4 | 29.6 |
| 4 | 5% Lutensol ® XL 30 | 4% $Al_2(SO_4)_3$ | 29.6 | 31.2 | 45.5 | 44.7 | 19.8 | 23.5 |

Hysorb ® F: superabsorbent polymer (BASF Aktiengesellschaft, Germany)
Lutensol ® XP 30: ethoxylated $C_{10}$-alcohol (BASF Aktiengesellschaft, Germany)
Lutensol ® XL 30: ethoxylated unsaturated $C_{10}$-alcohol (BASF Aktiengesellschaft, Germany)

TABLE 2

Concentration dependence

| Example | Surfactant solution | Cation solution | BA, moist [g/g] | FSC, dry [g/g] | CRC, dry [g/g] |
|---|---|---|---|---|---|
| 5 | 0.5% Lutensol ® XL 40 | | 11.8 | 36.3 | 27.5 |
| 6 | 1% Lutensol ® XL 40 | | 20.5 | 36.3 | 27.0 |
| 7 | 5% Lutensol ® XL 40 | | 21.8 | 36.6 | 27.6 |
| 8 | 0.5% Lutensol ® TO 3 | | 12.7 | 38.0 | 29.5 |
| 9 | 1% Lutensol ® TO 3 | | 16.3 | 37.0 | 29.6 |
| 10 | 5% Lutensol ® TO 3 | | 20.1 | 36.5 | 29.7 |

Lutensol ® XL 40: ethoxylated unsaturated $C_{10}$-alcohol (BASF Aktiengesellschaft, Germany)
Lutensol ® TO 3: ethoxylated iso-$C_{13}$-alcohol (BASF Aktiengesellschaft, Germany)
Examples 11 to 16
The tests were carried out similarly to Examples 1 to 10. The stated amount of surfactant solution, based on absorbing polymer, was sprayed on as a 25% by weight solution

TABLE 3

Solvent influence

| Example | Surfactant solution | Solvent | BA, moist [g/g] | FSC, dry [g/g] | CRC, dry [g/g] |
|---|---|---|---|---|---|
| 11 (comp.) | 0.25% Tween ® 20 | water | 8.8 | 40.0 | 30.7 |
| 12 (comp.) | 0.5% Tween ® 20 | water | 5.2 | 39.0 | 30.4 |
| 13 (comp.) | 1% Tween ® 20 | water | 9.1 | 40.1 | 27.7 |
| 14 (comp.) | 5% Tween ® 20 | water | 7.6 | 43.3 | 26.4 |
| 15 | 1.25% Tween ® 20 | DEGMBE | 17.7 | 21.9 | 16.9 |
| 16 | 2.5% Tween ® 20 | DEGMBE | 19.5 | 21.4 | 16.5 |

Tween ® 20: ethoxylated sorbitan monolaurate (ICI Ltd., UK)
DEGMBE: diethylene glycol monobutyl ether

We claim:

1. Polymeric particles capable of absorbing blood and or body fluids comprising
   a) at least one interpolymerized ethylenically unsaturated acid-functional monomer,
   b) at least one interpolymerized crosslinker,
   c) optionally one or more interpolymerized ethylenically and/or allylically unsaturated monomers copolymerizable with a),
   d) optionally one or more water-soluble polymers onto which said monomers a), b), and optionally c) are at least partially grafted, and
   e) optionally one or more reacted postcrosslinkers,
   wherein said polymeric particles are coated with at least one surfactant and with at least one solvent of the general formula (I)

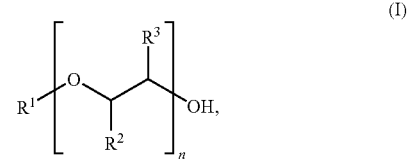

wherein
$R^1$ is $C_1$-$C_6$-alkyl with or without halogen substitution,
$R^2$ and $R^3$ are independently hydrogen or methyl, and
n is an integer from 1 to 5,
wherein the polymer particles are further coated with aluminum cations.

2. The polymeric particles of claim 1 wherein the surfactant is a nonionic surfactant having an HLB value in the range from 2 to 18.

3. The polymeric particles of claim 1 wherein the solvent is a compound of the general formula (I) wherein
$R^1$ is $C_2$-$C_o$-alkyl,
$R^2$ and $R^3$ are each hydrogen, and
n is an integer from 1 to 3.

4. The polymeric particles of claim 1 characterized by a blood absorbence of at least 15 g/g in the dry state.

5. The polymeric particles of claim 1 that are free of postcrosslinking.

6. A mixture of polymeric particles of claim 1 wherein not less than 20% by weight of said polymeric particles are free of postcrosslinking.

7. The polymeric particles of claim 1 wherein the polymeric particles are coated with a solution of the aluminum cations.

* * * * *

UNITED STATES PATENT AND TRADEMARK OFFICE
CERTIFICATE OF CORRECTION

PATENT NO. : 7,867,623 B2
APPLICATION NO. : 10/577028
DATED : January 11, 2011
INVENTOR(S) : Antje Ziemer et al.

It is certified that error appears in the above-identified patent and that said Letters Patent is hereby corrected as shown below:

In the Claims:

At Column 12, line 53, "$C_2$-$C_O$-alkyl" should be -- $C_2$-$C_6$-alkyl --.

Signed and Sealed this
Eleventh Day of October, 2011

David J. Kappos
*Director of the United States Patent and Trademark Office*